(12) United States Patent
Madariaga et al.

(10) Patent No.: US 8,663,715 B2
(45) Date of Patent: Mar. 4, 2014

(54) **COMPOSITIONS, PRODUCTS, THERAPEUTIC USES AND PROCEDURES FOR THE PRODUCTION AND/OR CRYSTALLIZATION OF EXTRACTS OF *ENCELIA CANESCENS* LAM (CORONILLA DE FRAILE)**

(75) Inventors: Edmundo Quevedo Madariaga, Santiago (CL); Carlos Quevedo Madariaga, Santiago (CL); Luis Quiñones Sepúlveda, Santiago (CL)

(73) Assignee: Naturaleza Y Fe Ldta, Santiago (CL)

( * ) Notice: Subject to any disclaimer, the term of this patent is extended or adjusted under 35 U.S.C. 154(b) by 0 days.

(21) Appl. No.: 13/578,317

(22) PCT Filed: Jan. 28, 2011

(86) PCT No.: PCT/CL2011/000009
§ 371 (c)(1),
(2), (4) Date: Oct. 11, 2012

(87) PCT Pub. No.: WO2011/097750
PCT Pub. Date: Aug. 18, 2011

(65) Prior Publication Data
US 2013/0028997 A1  Jan. 31, 2013

(30) Foreign Application Priority Data
Feb. 10, 2010 (CL) .................................... 119-2010

(51) Int. Cl.
*A61K 36/00* (2006.01)

(52) U.S. Cl.
USPC ......................................................... 424/725

(58) Field of Classification Search
None
See application file for complete search history.

(56) References Cited

PUBLICATIONS

Bohlmann et al, Dimeric chromenes and mixed dimers of a chromene with euparin from *Encelia canescens*, Phytochemistry, 22 (2): 557-560, 1983.*

* cited by examiner

*Primary Examiner* — Qiuwen Mi
(74) *Attorney, Agent, or Firm* — Gottlieb, Rackman & Reisman PC (57) ABSTRACT

The present invention relates to a composition containing extracts of *Encelia canescens* Lam and to aqueous or ethanolic extracts obtained therefrom, the procedure for the obtainment and crystallization thereof, and the uses thereof for the prevention and treatment of cancer, for example cancer of the pancreas, gastric tract, prostate, breast, kidney, colon, lung, vesicle, uterus, oral cavity, colorectal region, bladder, liver, brain tumors, and chronic and acute leukemia, in addition to metabolic diseases such as diabetes mellitus types I and II, viral and bacterial diseases, in particular related to *E. coli, Kiebsiella, M. flavus, S. aureus* and *B. subtilis*. Furthermore the use thereof is claimed in diseases related to oxidative stress and as a useful agent in the preparation of analgesics.

15 Claims, 10 Drawing Sheets

Figure 1

EHEX: Extract hexane
HEX: Hexane
EDCM: Extract Dichloromethane.
DCM: Dichloromethane.
EETAC: Extract ethyl acetate.
EMEOH: Extract methanol.

Figure 2

DCM: Dichloromethane.

Series 1 = Control (arabic gum 5%)

Series 2: Treated (methanolic extract in arabic gum 5%)

COMPOSITIONS, PRODUCTS, THERAPEUTIC USES AND PROCEDURES FOR THE PRODUCTION AND/OR CRYSTALLIZATION OF EXTRACTS OF *ENCELIA CANESCENS* LAM (CORONILLA DE FRAILE)

BACKGROUND OF THE INVENTION

For thousands of years the wisdom took into account properties of the plants or substances derived from these. At first intuitively through experimentation to determine which plants were toxic and which do not. The use of medicinal plants goes back to the time of Hippocrates (460-370 BC), who compiled a book containing information on more than 400 medicinal plants and your prescription. Even facts that indicate that from the year 2100 BC, the Mesopotamian civilization used medicinal plants have been found. At the evolution of the pharmaceutical industry, herbal medicine had a new flourishing, especially in developing countries, where today is a valuable source for a large number of active principles.

Currently popular medicine seems to have made peace with the herbal and before they were "obsolete herbs" for some, they have become great allies for the creation of the so-called phyto-pharmaceuticals. These are drugs made with natural ingredients obtained through modern technologies of industrial production and containing a standardized extract of a plant that is its component biologically active (active ingredient).

The use of these drugs seeks to achieve the relief of numerous pathologies as medicinal plants are not only plant tissue, since their cells hide chemical compounds with high therapeutic capacity. Current laboratory techniques allow to know the active principles of plants and provide a scientific basis to explain the basis of its ability to pharmacotherapy. The plants currently have direct and indirect use, when used indirectly is to obtain active molecules that provide chemical models in the synthesis of new drugs. The direct use is what is known as phytotherapy or the therapeutic application of drugs obtained directly from pulverized medicinal plants or simple extracts.

Medicinal products made from plants tend to be crude extracts, chromatographic fractions, mixes, or sets of compounds whose pharmacological action depends on the combination of the active ingredients obtained from the plant.

The phytopharmacology brings together ancestral ethnobotanical and etnomedical knowledge; these aspects joins to the modern basic and clinical pharmacological knowledge. Keeping the use of the medicinal plant, now in the form of standardized extract and backing it up with all the pharmaceutical technology available today, is a product that does not differ in their appearance and quality with traditional allopathic medicines.

The phyto-pharmaceuticals must not be contrasted with other drugs, but it must be a valid alternative in certain moments of the evolutionary process of the disease. They can even supplement, provided that this will benefit the patient.

Cancer

Cancer is produced by a cell that has lost its normal control mechanisms and that acquires therefore an uncontrolled growth. It can develop from any tissue in any organ. As the tumor cells grow and multiply, they form a mass of cancerous tissue that invades adjacent tissues and can "branch" by the body (metastasis). In Chile, this disease is the second leading cause of death (21.8 percent of the total) and continuously on the rise, the most relevant being the stomach, lung and prostate cancer among men, and gall bladder, stomach, breast and cervix among women (Medina E & Kaempffer A, 2001).

Diabetes

Diabetes Mellitus (DM) is a chronic disease of various etiologies characterized by hyperglycemia resulting from a deficit in the secretion or insulin action. Chronic hyperglycemia generated in this disease affects, in the long term, the development of nephropathy, retinopathy, neuropathy and cardiovascular complications, what determines high morbidity and mortality of patients with diabetes compared to the general population.

Diabetes Mellitus type 1 (DM1) is characterized by destruction of pancreatic beta cells, which translates into an absolute deficit of insulin and vital dependence from exogenous insulin. It occurs at any age, but its highest incidence is seen under 15 years of age with greater frequency in age pre-school and especially pre-puberty. Etiology in 90% is autoimmune, which is determined by the presence of antibodies (ICA), antiGAD and anti-insulin anti islets. 10% of the cases are idiopathic (technical guide, Diabetes Mellitus type 1, 2005, Chile).

The prevalence rate estimated by the World Health Organization (WHO) for the year 2000 is a 6.5%. Taking into account the number of people with DM1 under control in the National System of Health Services of the Ministry of Health (MINSAL), of approximately 3,000 (children and adults), estimated a prevalence of DM type In Chile of 0.5% of the diabetic population, significantly lower than the overall estimates (4 and 6%).

Diabetes mellitus type 2 is characterized by insulin resistance, usually accompanied by a relative deficit of insulin (technical guide, Diabetes Mellitus type 2, 2005, Chile). This is a little symptomatic disease, so its diagnosis is performed in about 50% of cases by laboratory tests requested by other causes and not by clinical suspicion. The scarce classical symptomatology determines that are belatedly diagnosed and in the presence of chronic complications with high frequency. This type of diabetes increases with age, obesity, and physical inactivity and is usually associated with other pathologies of high cardiovascular risk such as hypertension and dyslipidemia, so it is suitable to do research of DM in these individuals.

By the year 2000 it is estimated that more than 35 million people were suffering from DM on our continent, 54% corresponds to Latin America and the Caribbean (LAC) with a projection to 2025 of 64 million, rising to 62% in our region.

Both disorders described above with bacterial and viral diseases make up about 80% of recurring diseases in the world. In this regard, many products obtained from plants have approached resolve these pathologies, investing large amount of financial and human resources in this.

BACKGROUND OF THE INVENTION

Surprisingly, the inventors of this request have found excellent pharmacological properties of extracts of the plant *Encella canescens* Lam, particularly in the treatment of malignancies, diabetes and some microbial diseases and therefore this application raises the provision of compositions, extracts, products, and procedures of obtaining and/or crystallization of these extracts from plants for therapeutic purposes as a technical problem. *Encelia canescens* Lam (nv: mancapaqi, mataloba, matalobo, mucle). It is a perennial subshrub of 30-80 cm high, erect, pivot root, stem green grey by the presence of white hairs and very branched. Leaves alternate, petiolate, oblong entire edge of 37 cm long, with three nerves marked, most grouped near the base of the plant, which grows between the Atacama and Coquimbo (II-IV region), up to 1,700 m above sea level.

The marginal and ligulate flowers are female and yellow; the central and tubular flowers, brown, pentajagged, with a receptacle gamosepalous calicino (without teeth) that surrounds the ovary, and a tuft of white hair; stamens with anthers united; inferior ovary with style divided into 2 hairy branches. The fruit is an achene 5 mm long with the pubescent faces (Linares et al, 2000).

By the physiological characteristics of the plant become a species not very desired by pests and diseases, presents somewhat hard leaves, slightly pubescent and both tough, stem slightly lignified.

In order to not alter its medicinal properties, in the presence of any vector his attack should be placated with natural health products as for example concentrated tobacco, onion or garlic juice, etc. Any product that is friendly with the plant and the environment.

In the seedling stage is where the plant is more vulnerable to attack by pests and diseases, the control should be only with products of action by contact, because systemic products produce leaf abortion or the death of the seedling.

In the literature, pharmacological studies for this species are not found, only a chemical study of cromenos dimmers is found (Bohlmann et al., 1983) and botanical studies (Brako and Zarucchi 1993; Zuloaga and Marrone, 1996). To the peruvian species (mancapanqui) they attributed galactophore properties and the infusion is used in urine retention problems (Pastor et al. 1996). In other species of the genus they are used for toothache pain and as an analgesic (Moerman 1998).

EXAMPLES

The following examples are preferred but not exclusive of other protected aspects of the invention:

Example 1

Preparation of Extracts

The aerial part of Encelia ranescens Lam was collected in the Region III Valley River Huasco, Chile. A sample witness of the plant identified at the Faculty of Chemical and Pharmaceutical Sciences of the University of Chile is preserved at the international Herbarium "Herbarium of the School of Chemistry and Pharmacy (SQF) of the Faculty of Chemical and Pharmaceutical Sciences, University of Chile, under No. 22,259."

Two different samples have been investigated:
A.—Dry and ground sample
B.—Fresh leaves of the plant
Which were processed as described below:
A.—The Sample Dried and Ground is the Sample on which all Tests were Made.

The dried and ground sample (871 g) was subjected to different processes for obtaining of extracts at ambient temperature using the method of successive extractions by solvents increasing polarity, the extraction of essential oil, and the global methanol extract.

Sequential extraction by increasing polarity with solvents hexane, dichloromethane and methanol, allowed to obtain the extracts: hexanic (EHEX), dichloromethane (EDCM) and sequential methanol (EMETS).

Figure 1:
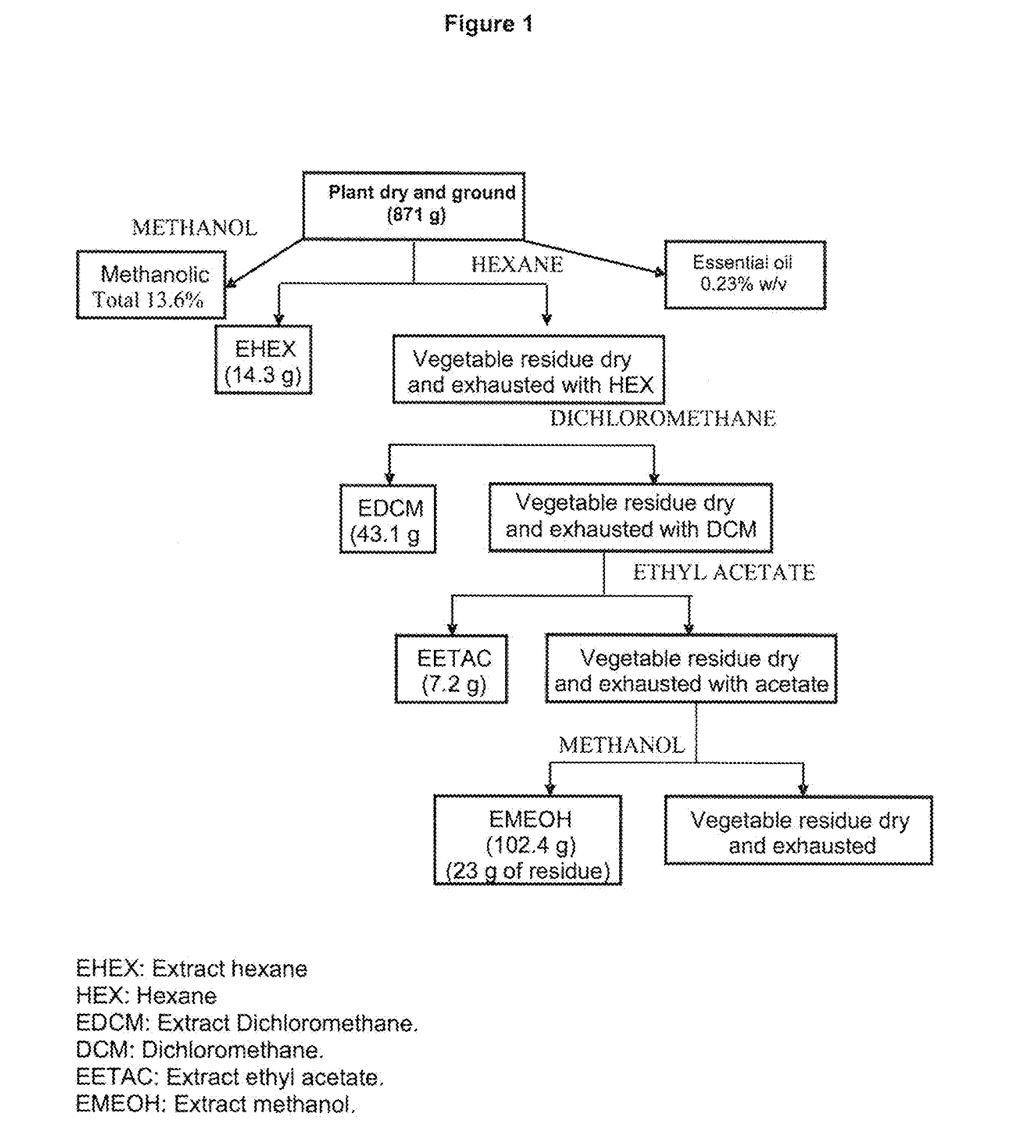
FIG. 1: Scheme of extraction of dry extract of *Encelia canescens* Lam.

The essential oil was obtained by drag with vapour of water procedure. To do this the sample is placed in an extractor equipped with a device of Clevenger, heating up at least 3 hours followed. After this time the amount of oil extracted was measured, retired, dried with anhydrous sodium sulphate and re-packaged in dark container in nitrogen atmosphere and stays away from the light and refrigerated until used (FIG. 1).

B.—Fresh Leaves of the Plant

Figure 2:
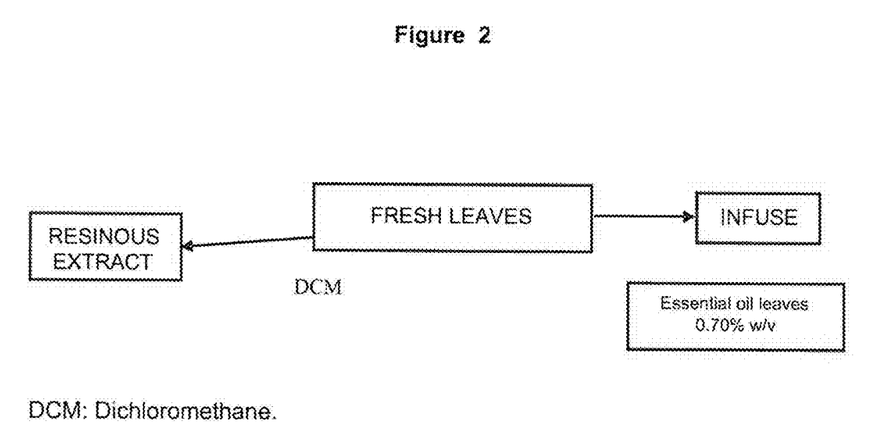
FIG. 2: Scheme of extraction of fresh leaves of *Encelia canescens* Lam.
Figure 3:
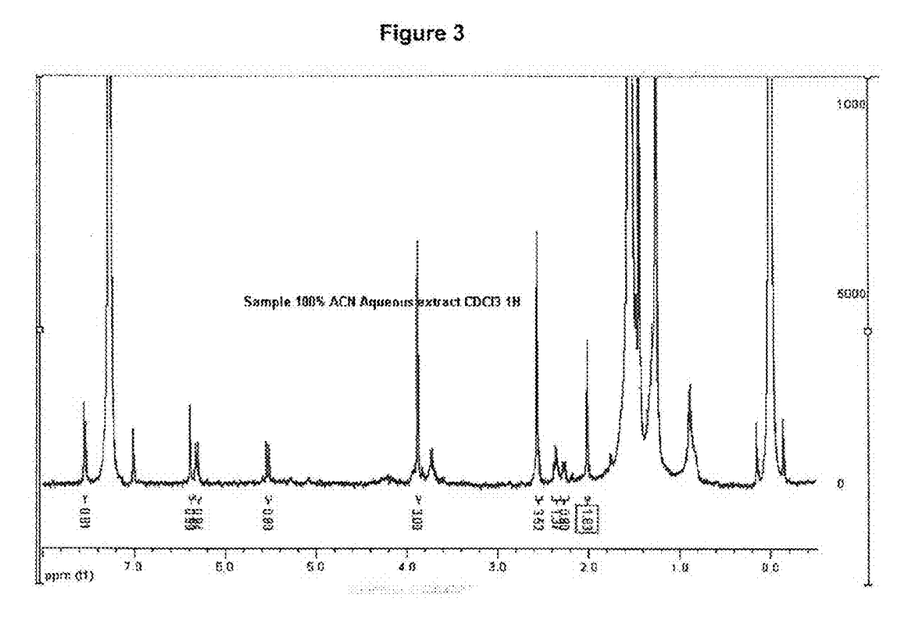
FIG. 3: Unibidimensional proton nuclear magnetic resonance spectrum of aqueous extract of *Encelia canescens* Lam.
Figure 4:
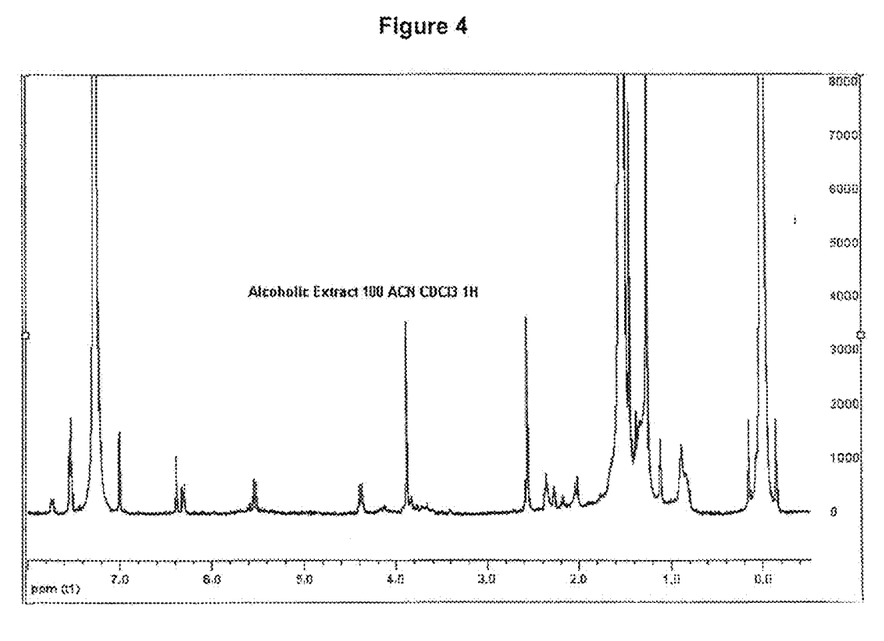
FIG. 4: Unibidimensional proton nuclear magnetic resonance spectrum of ethanolic extract of *Encelia canescens* Lam.
Figure 5:
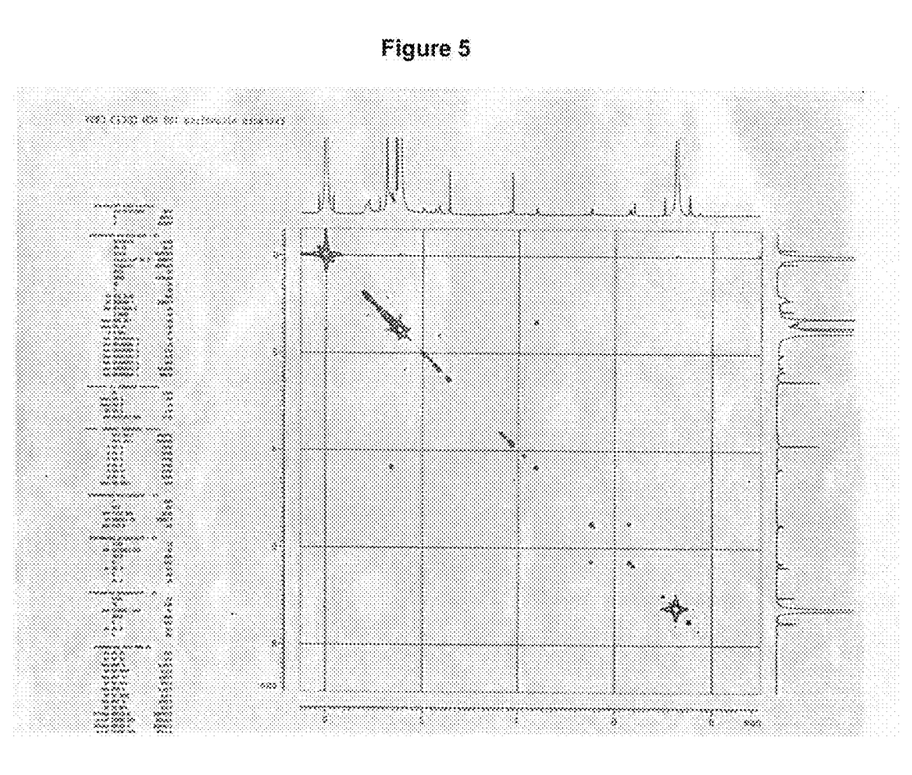
FIG. 5: Two-dimensional proton nuclear magnetic resonance spectrum (COSY) of aqueous extract of *Encelia canescens* Lam.
Figure 6:
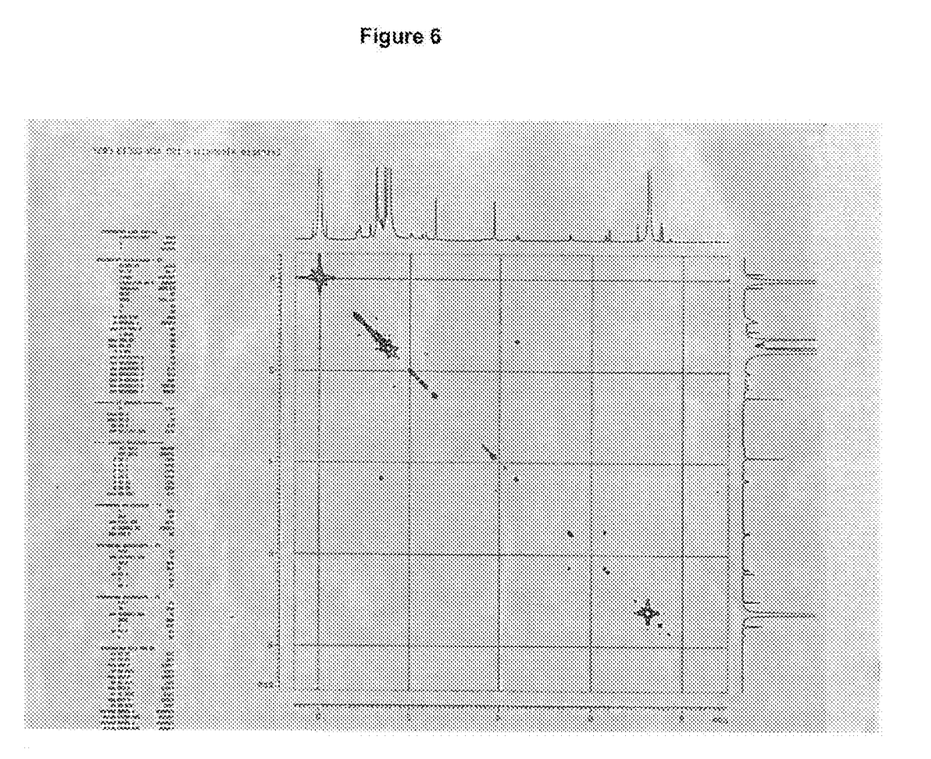
FIG. 6: Two-dimensional proton nuclear magnetic resonance spectrum (COSY) of ethanolic extract of *Encelia canescens* Lam.
Figure 7:
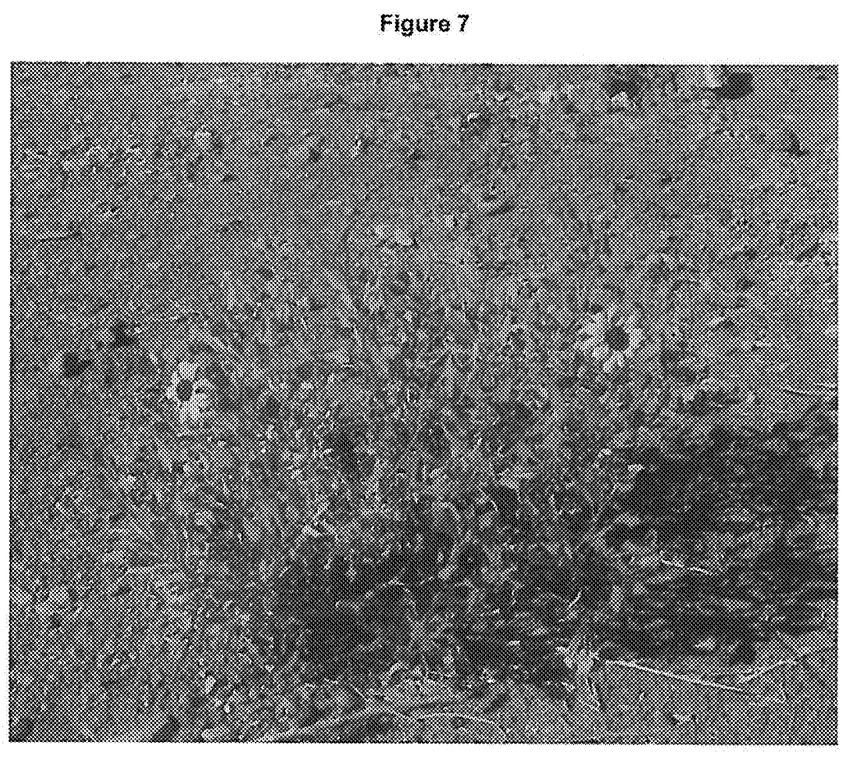
FIG. 7: Photograph of the complete plant of *Encelia canescens* Lam.

From the fresh leaves, the resinous exudate, the essential oil and the infuse was obtained. The resinous exudate of the plant was extracted from fresh leaves by soaking them at room temperature in dichloromethane (DCM) and renewing the solvent up to total removal, getting the extract of the resinous exudate (ERE). Essential oil was obtained by the same procedure as for sample A (FIG. 2).

The infuse 10%, was obtained from the leaves of the plant dry and ground, which were weighed and then added water boiling leaving 10 minutes at rest, it then proceeds to filter to get the infuse (INF).

Each successive extraction was performed to total exhaustion, leaving between each, dry the plant at room temperature before adding the new solvent.

All extracts were taken to dryness, until total elimination of solvent, to be subjected to the pharmacological and microbiological tests.

Example 2

Physicochemical Characterization of Extracts

A phytochemical tracing of the different extracts and the infuse of a canescens by thin layer chromatography (t.l.c.) was made, to investigate the presence of secondary metabolites, using silica gel G chromatolamines type 60 with fluorescence indicator (Merck S.A.). Used mobile phases were mixtures of solvents, which achieved the best separation allowing to visualize the different chemical groups of constituents of the extract or infuse, the chromatograms were revealed with different reagents and they were also analyzed to UV light at 254 and 366 nm wavelengths.

Table 1 shows mobile phases used and in Table 2 are brought developers reagents and patterns.

TABLE 1

| Mobile phases used in the t.l.c. | |
|---|---|
| Mobil phase | Detected chemical groups |
| DCM 100% | Triterpenes-Sterols Terpenes |
| DCM:EtAc (9.1) | Alkaloids Anthraquinones |
| DCM:EtAc (1.1) | Flavonoids |
| EtAc:MeOH (7.3) | Coumarins |

DCM: Dichloromethane
EtAc: Ethyl acetate
MeOH: Methanol

TABLE 2

| Developers reagents and patterns used in t.l.c. | | |
|---|---|---|
| Secondaries metabolites | Pattern substance | Developer reagent |
| Alkaloids | — | Dragendorff |
| Triterpenes-Sterols | Oleanolic acid/ β-sitosterol | Lieb.-Bürchard y p-anisaldehído |
| Anthraquinones | — | Börntrager |
| Flavonoids | quercetin-kaempferol | Light UV, NP/PEG, $AlCl_3$ y $NH_3$ |
| Terpenes | — | p-anisaldehyde |
| Coumarins | Scopoletin | Light UV: $AlCl_3$ y NP/PEG |

Tannins were identified with the EMET, ERES and the INF dissolved in distilled water by adding one or two drops of $FeCl_3$, the ERES was dissolved in methanol.

Through the use of the foam index the presence of saponins (substances with surface-active properties) was detected through the formation of persistent foam (for 15 min), using a 1 g drug or dry plant extract in an appropriate volume of distilled water. The saponins search was conducted in the EMET and INF dissolved in distilled water by shaking for 5 min and leaving to, stand for 15 min, observing the formation of homogeneous and persistent foam.

Table 3 lists the results of the analysis of physical-chemical tracing:

TABLE 3

Result of identification tracing by c.c.f. extracts and infuse.

| Secondary Metabolite | Developer | ERES | EHEX | EDCM | EACET |
|---|---|---|---|---|---|
| Alkaloids | Dragendorff | − | − | − | − |
| Sterols and triterpenes | Liebermann Burchard | + | + | + | + |
| Anthraquinone | Böntrager | − | − | − | − |
| Flavonoids | NP/PEG | + | + | + | + |
| Coumarins | NP/PEG | ± | + | + | + |
| Tannins | FeCl$_3$ | − | − | − | + |
| Saponins | Foam | − | − | − | − |

| Secondary Metabolite | EMEOH | INFUSE |
|---|---|---|
| Alkaloids | − | − |
| Sterols and triterpenes | + | − |
| Anthraquinone | − | − |
| Flavonoids | + | + |
| Coumarins | ± | − |
| Tannins | + | + |
| Saponins | − | + |

Chemical Analysis of Essential Oil

This analysis was carried out by gas chromatography associated with mass spectrometry in a GC Fisons equipment, with a volume of injection of 1 μl in different chromatographic conditions, with the aim of promoting the volatilization of the compound contained in the sample. Conditions finally selected were: "Carrier" Gas: helium, temperature 70° C. (4 min) initial, 100° C./min, 2000° C. (1 min) 200° C./min, 3,000° C. (2 min.) Injector temperature 2,500° C.

The identification of compounds took place by means of the comparison of the obtained mass spectra with those of the data base controlled by the computer (data base NIST).

The analysis of the essential oil indicates that it is in smaller proportion in the dry sample (approximately ⅓) with respect to the leaves.

This would indicate that with time a possible loss of this substance or participation of other substances that do not display these properties authenticated by the great amount of solids found in the sequential methanol extract.

The tracing indicates presence of diverse substances, specially terpenes and/or steroids in addition to flavonoids, coumarins and tannins. Also it indicates the absence of alkaloids and anthraquinones according to the general reagents of identification.

The dry and ground sample presents great amount of solid (possible polysaccharide) that is not observed in the leaves of the plant (around 20% in weight). This difference is reflected in the essential oil in which it is observed that the dry sample presents approximately ⅓ of the amount of the essential oil of the leaves.

Analyses of the Extracts by Means of Nuclear Magnetic Resonance Spectroscopy 50 mg of *Ericalia canescens* Lam aqueous and ethanolic extracts were dissolved in nanopure water/ethanol 20%, 1 ml for aqueous sample and 10 ml for the ethanolic sample. Non-dissolved rest was eliminated by means of centrifugation and the samples were loaded in disposable C-18 Sept-pack columns (Waters). The columns were washed with 10 ml of water and they were eluted with 2 fractions of acetonitrile (70 and 100%). Each fraction was collected separately and took to dryness at vacuum by means of a CentriVap Console (Labconco) to 75° C. The samples were resuspended in deuterated chloroform or deuterated dimethyl sulfoxide and analyzed by means of unidimensional and bidimensional nuclear magnetic resonance spectroscopy of the aqueous and ethanolic extracts (FIGS. 3, 4, 5 and 6) in a Bruker 400 MHz Avance equipment.

The analysis of the obtained NMR spectra shows the presence of tetracoumarin with the formula In addition, a terpene with the following chemical structure is found:

On the other hand, the presence of an anthocyanin like tannin with the following general formula was also found:

Example 3

Inhibition of Tumor Cell Growth

The experiments were developed on the SaOS-2 cell line, not transformed cell line derived from human osteogenic sarcoma (American Type Culture Collection ATCC®: HTB-85 German Collection of Microorganisms and Cell Cultures DSMZ®: ACC 243).

The cells were maintained in McCoy's 5A medium supplemented with 15% bovine fetal serum (BFS), 100 U/ml of penicillin, 0.07 mM of streptomycin (Gibco®), 0.5 µM of amphotericin B (Gibco®) and 2 mM of L-glutamine (Gibco®). Incubated to 37° C. with an atmosphere of air 95% and CO 5%. The culture medium was renewed every 48 hours.

Once the cells reached a condition of sub-confluence (80 to 90% of confluence) in the culture plates, culture medium was withdrawn and adhered cells were washed with PBS (phosphate buffer saline) to 37° C. and then treated with 1 ml of trypsin solution 0025% EDTA 0.5% for plate of 60 cm$^2$ (and 250 µl for plates of 10 cm$^2$) during 2 minutes to 37° C., adding subsequently equal volume of culture medium supplemented with the purpose of arresting the hydrolytic reaction catalyzed by trypsin. After trypsinization, all the cells were peeled from the culture plate by means of slight agitation and transferred to a sterile tube (Falcon® or Eppendorf®), then they were subjected to centrifugation (1,000 rpm during 10 minutes to 25° C.), the supernatant was eliminated and the cellular "pellet" was conserved. Next, "pellet" obtained was resuspended in a determined volume of supplemented medium and 10 µl from this homogenous suspension were taken for the accomplishment of the cellular counting in Neubauer chamber, quantifying the number of cells in optical microscope (objective 10×). Also the cellular viability by means of stain with Trypan Blue 0.5% (No. alive cells [not dyed]/No. total cells) was evaluated. All cellular count from a determined suspension was made in triplicate.

In order to make the study of cellular proliferation, the cells quantified and obtained, seeded in identical amounts in 10 cm$^2$ culture plates (8×10$^4$ cells by plate, specifically 79.167±8.036), with 2 ml of supplemented culture medium. In these conditions the SaOS-2 cells reach confluence approximately between the 96 to 120 hours of culture. Five study groups were generated according their treatment:

1) Without treatment; control group
2) Aqueous extract (final concentration in the culture, fcc: 1%)
3) Dispersing phase of the aqueous extract (water) (fcc: 1%)
4) Ethanolic extract (fcc: 0.5%)
5) Dispersing phase of the ethanolic extract (ethanol) (fcc: 0.5%)

The final concentrations used in the different groups were established from previous experiments made in the same cellular line, where they demonstrated not to be able to generate quantifiable cellular death, and therefore they are used with the purpose of evaluating its effect in the cellular proliferation, discarding an acute toxic effect on the viability of the cells (SaOS-2) in culture.

A protocol to evaluate the profile of growth of the different cellular groups in study was established, this consisted of making cellular counts from three plates for each group, at regular intervals of 24 hours, including a total monitoring of 5 days (times established for the cellular count: 0, 24, 48, 72, 96 and 120 hours). After 48 hours of culture (time 48 and 96 hours for this protocol), all the cellular groups are subjected to renovation of their culture media with the incorporation of the extracts and/or dispersing phases that correspond according to each group and in the same established conditions.

For descriptive statistical conventional methodologies were used, and all of the data were expressed as averages±standard deviation (SD) of at least three independent counts. The comparative analysis between the averages±SD of the measured variables, was determined using the test t of independent samples, and $p<0.05$ was considered statistically significant.

Figure 9:
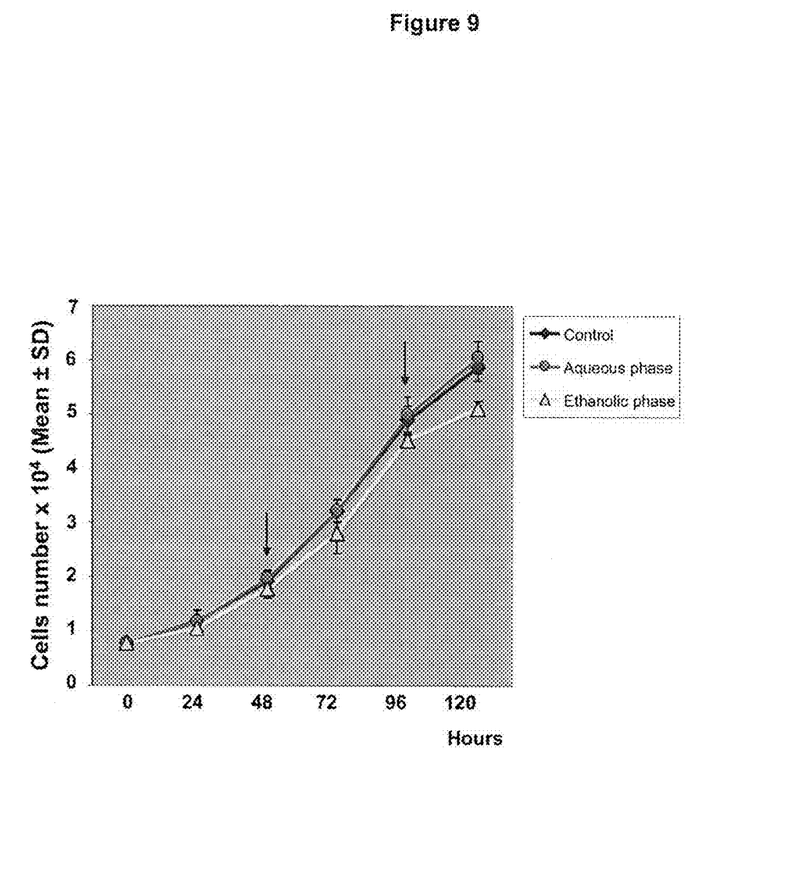
FIG. 9: The in vitro proliferative activity of SaOS-2 cells, is unaffected by low concentrations of aqueous (1% water) and ethanolic (ethanol 0.5%) phases, used in the extractions of *Encelia canescens* Lam. The arrows indicate time at which the renewal of culture media was made, keeping the treatments and their respective concentrations.

Significant differences between the groups control (No. 1), treated with aqueous phase (No. 3) and treated with ethanol phase (No. 5), were observed, therefore the effect of liquid phases of extraction (aqueous and ethanol) on the proliferative activity of SaOS-2 cells is discarded, to the concentrations used in this protocol (FIG. 9).

Figure 10:
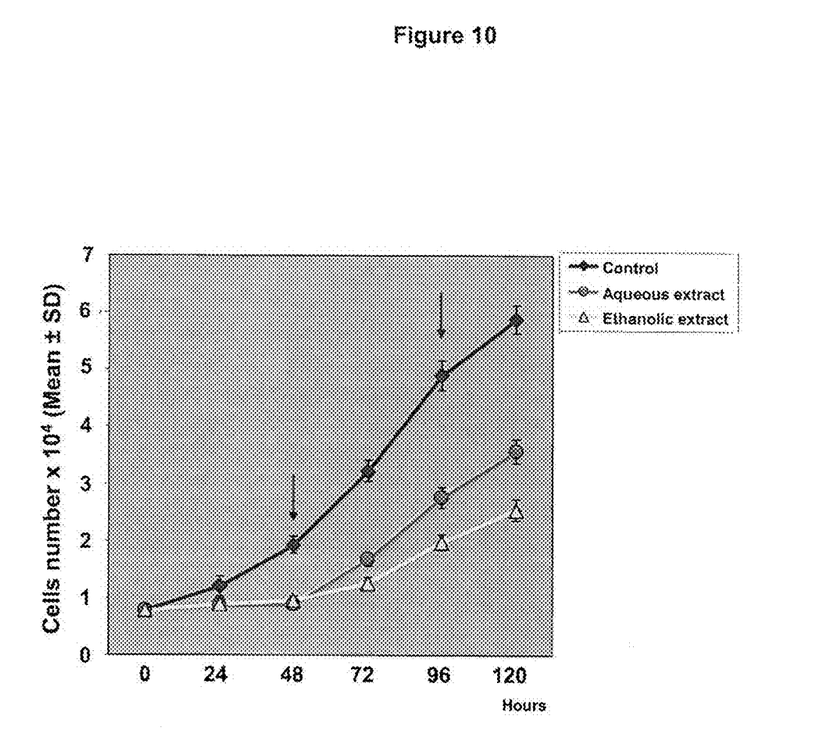
FIG. 10: Repressive effect on in vitro proliferative activity of SaOS-2 cells, produced by treatment with aqueous and ethanolic extracts of *Encelia canescens* Lam. The arrows indicate time at which the renewal of culture media was made, keeping the treatments and their respective concentrations.

The comparative analysis between the cellular counts for the groups of cells treated with the extracts (aqueous and ethanol) shows a significant difference (values of $p<0.001$), indicating that such treatments diminish the proliferative activity of these cells (FIG. 10).

TABLE 4

Detail of the count of cells (averages ± SD) obtained every 24 hours until a total of 5 days (120 hours), for the five groups in study.

| Groups | Time of counts (hours) | | | | |
|---|---|---|---|---|---|
| | 24 | 48 | 72 | 96 | 120 |
| 1) Control | 120,000 ± 17,500 | 193,333 ± 14,216 | 322,500 ± 18,875 | 490,000 ± 26,101 | 587,500 ± 24,622 |
| 2) Aqueous Extract | 87,500 ± 6,614 | 89,167 ± 8,780 | 167,500 ± 11,456 | 275,833 ± 18,764 | 357,500 ± 21,360 |
| 3) Aqueous Phase | 118,333 ± 20,817 | 199,167 ± 13,769 | 322,500 ± 22,500 | 500,000 ± 32,787 | 605,833 ± 29,826 |
| 4) Ethanolic Extract | 90,000 ± 10,000 | 95,833 ± 7,638 | 125,833 ± 10,408 | 197,500 ± 13,010 | 254,167 ± 18,764 |
| 5) Ethanolic Phase | 105,833 ± 5,204 | 178,333 ± 17,017 | 281,667 ± 37,942 | 451,667 ± 10,104 | 511,667 ± 13,769 |

TABLE 5

Results of the comparative statistical analysis between the averages ± SD of the cellular counts obtained for the treated groups (groups 2, 3, 4 and 5), versus the control group (without treatment), using the test t. The values for t with 4 degrees of freedom and p value for every time of sampling (24, 48, 72, 96 and 120 hours) are shown. The results statistically significant ($p < 0.05$) are shown in gray bottom.

| Groups | Times | | | | |
|---|---|---|---|---|---|
| | 24 | 48 | 72 | 96 | 120 |
| 2) Aqueous Extract | 3.01 p = 0.04 | 10.80 p = 0.001 | 12.16 p = 0.001 | 11.54 p = 0.001 | 12.22 p = 0.001 |
| 3) Aqueous Phase | 0.11 p = 0.92 | -0.51 p = 0.63 | 0.00 p = 1 | -0.41 p = 0.70 | -0.82 p = 0.46 |
| 4) Ethanolic Extract | 2.58 p = 0.06 | 10.46 p = 0.001 | 15.80 p = 0.001 | 17.13 p = 0.001 | 18.65 p = 0.001 |
| 5) Ethanolic Phase | 1.34 p = 0.25 | 1.17 p = 0.31 | 1.67 p = 0.17 | 2.37 p = 0.08 | 4.66 p = 0.01 |

These data suggest that the presence in culture media of both aqueous (1%) and ethanolic (0.5%) extract, obtained from *Encelia canescens* Lam diminish in a way statistically significant the potential of proliferative growth of SaOS-2 cells in vitro, being the ethanolic extract slightly more efficient in this anti-proliferative effect. This guarantees the potential use of the extracts of plants in neoplastic diseases.

Example 4

Determination of Antioxidant Activity

The stem, the leaves and the flower dry and ground, were used for the extraction by means of the soxhlet method, with solvent, made with hexane and/or ethanol. The extract thus obtained was evaporated and some compounds are crystallized, being detected among them resins, flavonoids and other components to a lesser extent.

These crystals were washed with ethyl acetate, obtaining the total pure flavonoids, later treated by similar methods to isolate the flavonoid detected by spectroscopic analysis, to obtain a remanent with better antioxidant index.

150 gr from the grass dry and ground were taken and an extraction with solvent ethanol was made obtaining 17.2 gr of crystals, on which the purification was made.

The purification threw a total of 0.63 gr that corresponds to total flavonoids (all the types of flavonoids present enter here). Within this group, one with a probable structure of phenolic benzofurane little common and of very good stability, is detected. This flavonoid was isolated having been obtained an amount of 0.87 mg, which constituted a 0.42% of total flavonoids.

The antioxidant activity of index IC50 gives values of 4.8 mg/ml for the total flavonoids and of 1.5 mg/ml for the isolated flavonoid. These values are compared with a reference (Trolox), which has an index of 1.97 mg/ml, almost equal to the one of tocopherol (vitamin E) very used industrially.

In order to determine completely the antioxidant capacity, tests in other substrates, like oil and proteins, should be conducted, with the purpose of being able to determine in good form where direct markets penetration efforts.

Industrially the plants of extraction of antioxidants are not very complex, and of medium size.

It was observed that the antioxidant capacity of the isolated flavonoid is very good, surpassing the pattern. The isolated flavonoid has probably a benzofurane structure which gives it much stability achieving to inhibit the passage to pro-oxidant when catching free radicals. Even though the total flavonoids throw a higher index, will depend on the commercial approach that gives to products to be extracted industrially.

DPPH Test

The bioassay is based on that the radical 2,2-diphenil-1-picril hidrazile hydrated (DPPH) of intense violet color, when captured by free radical catcher compounds forms a colorless stable compound. With this it is possible to quantify the capturing capacity of free radicals that have different substances by means of the determination of the discolouring degree that these compounds cause to a methanolic solution of DPPH.

For it, a just prepared methanolic solution of DPPH 20 mg/ml was used. The methanolic extract in a range of concentrations of 1 to 200 µg/ml was used. According to the following protocol of Table 5, volumes of DPPH and solutions of the samples were mixed by triplicate, for after five minutes to read the absorbance in the spectrophotometer UNICAM to a 517 nm wavelength.

TABLE 6

Protocol of Assay of DPPH test
(2,2-diphenil-1-picril hidrazile hydrated)

|  | Sample | Blank sample | Control |
|---|---|---|---|
| Sample (µL) | 375 | 375 | 0 |
| DPPH (µL) | 750 | 0 | 750 |
| Methanol (µL) | 0 | 750 | 375 |
| Total volume (µL) | 1,125 | 1,125 | 1,125 |

The calculation of the percentage of discolouring (free radicals capturing capacity), was determined using the following formula:

% Discolouring=[1−($A$ compound/$A$ blank)]*100

A value equal to 100 corresponds to the highest free radicals capturing capacity and a value near to zero indicates a null capacity, reason why the discolouring degree indicates the efficiency of the substances as free radicals captors. As reference compound of free radicals captors quercetin was used in concentrations between 1.25 a 7.5 µg/ml.

Result: negative up to 200 µg/ml of the methanolic extract.

In addition, the antioxidant capacity was analyzed using the system lacase-ABTS (2,2-azino-bis-3-ethyl-benzo-thiazolin-6-sulfonic) that allows to establish in a comparative way the oxidation of substrates, denoting of indirect way the antioxidant capacity of a sample (Table 7).

TABLE 7

Antioxidant Evaluation in System ABTS
(2,2-azino-bis-3-ethyl-benzo-thiazolin-6-sulfonic)

| Data | Mass | % (c/r to the vegetable material) |
|---|---|---|
| Analyzed material | 150 g | 100 |
| Hexane extract | 6.2 g | 3.10 |
| Ethanol extract | 17.2 g | 4.10 |
| Total flavonoids | 0.63 g | 0.42 |
| Isolated flavonoid* | 0.87 mg | 0.06 |

| Antioxidant activity | $IC_{50}$ (mg/mL) |
|---|---|
| Hexane extract | >40 |
| Ethanol extract | 11.60 ± 0.10 |
| Total flavonoids | 4.80 ± 0.15 |
| Isolated flavonoid | 1.50 ± 0.02 |
| Trolox ® (reference) | 1.97 ± 0.06 |
| Ethanolic extract boldo leaves | 3.20 ± 0.78 |

The extracts and the fraction of flavonoids present an interesting antioxidant and potentially usable activity, since the power of the extract of flavonoids is comparable to the one of the antioxidant one of reference (Trolox®).

Example 7

Evaluation of the Antimicrobial Activity by the Bioassay Bioautography

For the accomplishment of this bioassay silica gel 60 (Merck) chromatograms of 5 cm wide by 7 cm height were made and the isolated fractions or compounds were seeded. The more appropriate mobile phase for each sample to assay was determined. Cultures of the microorganisms to assay were prepared in a liquid culture medium (TSB for bacteria and PDB for fungi and yeasts) with 24 hours and 48 hours of anticipation respectively. An aliquot of 1 ml of microorganisms was taken and resuspended in 9 ml of liquid culture medium, and was placed an orbital agitator to 37° C. by 2 hours, with the purpose of obtaining a culture in logarithmic phase of growth.

The chromatogram was exposed to UV radiation (λ 254 nm) for 30 minutes in order to be sterilized for later use. The suspension of the micro-organism was added to the molten solid culture medium into a sterile tube (ISA for bacteria and PDA far fungi and yeast). Suspension was mechanically homogenized using a stirrer and was added on the chromatogram, being covered thoroughly with the film of agar inoculated with each bacterium or fungus. Finally the chromatograms were placed each in sterile Petri dishes with top in a humid environment with sterile distilled water and incubated for 24 hours in an oven controlled at 37° C. for bacteria and for 48 hours at 28° C. for fungi. The bioautographies were revealed with a salt of tetrazolium (MIT) and were let incubating for 1 hour more. When developer reagent was added they turned with a deep violet colour, excluding the zone where there was inhibition of bacterial growth by the present active metabolites, leaving ivory coloured and to which their Rf was measured (Rahalison et al., 1991; Hamburger and Hostettman et al., 1991; Erazo at al., 1997).

TABLE 8

Evaluation of the Antimicrobial Activity by the Bioautography Bioassay

| Strain | Oil | Hexanic | DMC | Resin | EtoAc | Metha-nolic s. | Metha-nolic g |
|---|---|---|---|---|---|---|---|
| P. aeruginosa | − | − | − | − | − | − | − |
| E. coli | + | + | + | + | − | − | + |
| Klebsiella | − | + | + | + | − | − | + |
| S. aviatum | − | − | − | − | − | − | − |
| M. flavus | + | + | + | − | − | − | + |
| S. aureus | − | + | + | + | − | − | + |
| B. subtilis | + | + | + | + | − | − | + |
| Candida | − | − | − | − | − | − | − |
| Sacharomyces | − | − | − | − | − | − | − |

Mobile phase: DCM/Et Ac 7:3 only the S. aureus DCM/Et Ac 9:1
Extracts: Et Ac, Methanolic s. Mobile phase: Et Ac/MeOH 7:3

The extract presents antibacterial activity against *E. coli, Klebsiella, M. flavus, S. aureus, B. subtilis*, especially the essential oil and nonpolar extracts (resin, hexane and dichloromethane) in both polar extracts, only the global methanolic presents antibacterial activity (table 8).

Example 8

Determination of Toxicological Activity

The in vivo biological study evaluated the toxicity, oral analgesic activity and topical analgesic activity in the global methanolic extract of *Encelia canescens* Lam. For these assessments not inbred males CF-1 strain mice were used, whose weight varied between 14 to 20 g and age between 30 to 35 days. In all evaluations, animals were kept in fasting for 12 hours prior to each test with water ad libitum at room temperature.

Each test was carried out with 10 animals, leaving 2 of them as controls, adding these to a "pool" of animal controls, in total were a group of 16 control animals. At the end of the tests, the animals were sacrificed by cervical dislocation, a painless method.

For all tests, the pharmacological effect was calculated using the values of the median, as a measure of central tendency of the data and standard error of the median (SEM) as measure of dispersion.

Results were analyzed by the non-parametric statistical method of Wilcoxon for independent data (Hollander and Wolfe, 1973), considering significant if its $p \leq 0.05$.

Oral Toxicity

The toxicity of global methanol extract of *Enceila canescens* Lam was evaluated, through the administration of 2 g/Kg of animal bodyweight, suspended in saline gum arabic to 5% in volume of 0.4 ml for mice of 25 g weight, through a 4 french gastric feeding tube. Animals were kept in observation for ten days with food, water and ambient temperature, controlling their weight on a daily basis.

Once administered the extract, appearance of clinical signs, morbidity and mortality should be observed. This observation was made during the early hours and then daily for the ten following days.

The necropsy of animals was performed once finished the period of observation, sacrificing them by cervical dislocation and making a macroscopic analysis of the principal organs in order to determine if there were alterations compared to control animals who received only saline solution of gum arabic 5%.

In the first 4 hours after administration of the global methanolic extract (GME) it could be observed in treated animals the following signs:

Motor signs: movements in normal form, absence of seizures, absence of fall of the rear train, absence of drowsiness.

Respiratory signs: absence of gasps and cyanosis.

Gastrointestinal signs: absence of emesis and diarrhea.

Salivation: absence.

Piloerection: absence.

Body weight obtained growth lower, but not significant with respect to the control.

After completing 10 days of observation and weighing daily, the animals were sacrificed by cervical dislocation, 2 randomly were chosen to perform the visual observation of the autopsy of the principal organs. The observed parameters were: color, texture, and size. These parameters were compared with those of control animals.

During the analysis of the animals treated with the extract of the plant not differences with respect to the color, size and texture, compared to the organs of animals corresponding to the control group, were found.

Based on these results it was concluded the safety of global methanol extract (GME) of *Encelia canescens* Lam at the doses used orally in mice. While in vivo experimental animal data are indicative of toxicity and are taken as safety markers, acute toxicity tests aren't enough to hold that the extract is non-toxic, as a frequent dosage and long-term effects are not considered, (WHO, Geneva, 1997).

TABLE 9

Comparison 10 days of observation.

|  | Days | SEM |
|---|---|---|
| Median |  |  |
| 17 | 1 | 0.74 |
| 22.45 | 2 | 0.9 |
| 23.45 | 3 | 1.04 |
| 24.25 | 4 | 1.38 |
| 24.45 | 5 | 1.59 |
| 26.3 | 6 | 3.61 |
| 28.55 | 7 | 3.95 |
| 29.3 | 8 | 4.04 |
| 29.95 | 9 | 4.16 |
| 31.1 | 10 | 4.26 |
| Controls |  |  |
| 17.3 | 1 | 0.27 |
| 24.05 | 2 | 0.59 |
| 25.25 | 3 | 0.71 |
| 26 | 4 | 0.73 |
| 26.55 | 5 | 0.91 |
| 27.35 | 6 | 1.01 |
| 30.05 | 7 | 1.2 |
| 31.1 | 8 | 1.33 |
| 31.8 | 9 | 1.3 |
| 32.8 | 10 | 1.48 |

In this comparative table, the ten days of observation versus median weights were graphed. As it can see mice had a growth lower but not significant with regard to controls, which demonstrates that the extract tested did not provide toxicity in them (FIG. 8).

Figure 8:
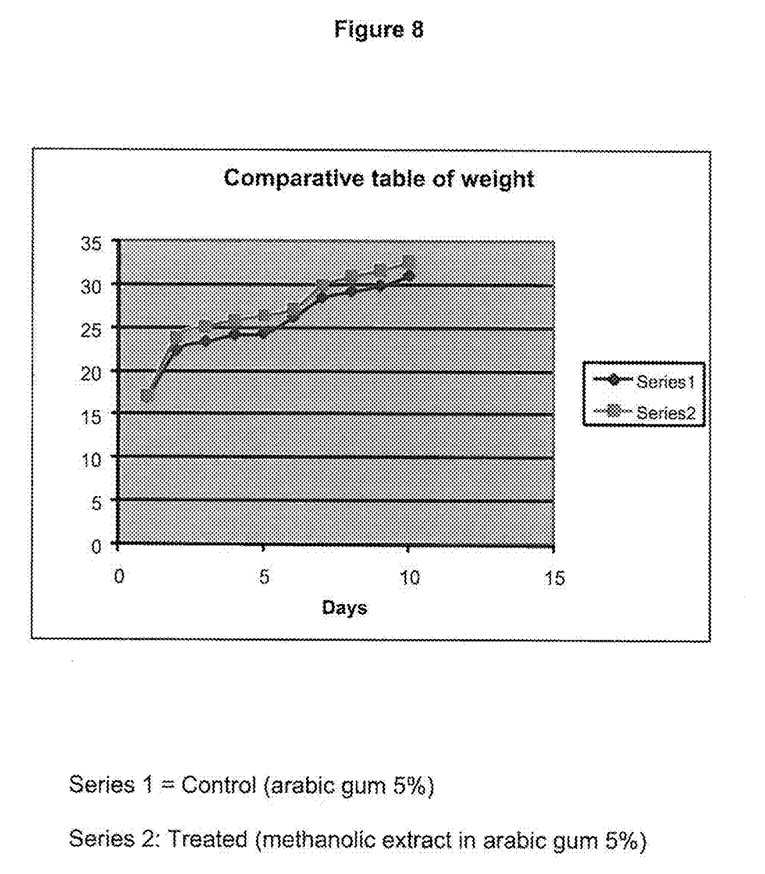
FIG. 8: Relation of day 1 weight gain with day 10, for this the median weight gain in mice that received the extract global methanol and controls without the extract was calculated.

The sample does not present acute toxicity based on the harmlessness of the global methanolic extract (GME) of *Encelia canescens* Lam at the doses used orally in mice, confirmed by necropsy and no modification of the body weight (Table 9 and FIG. 8).

Example 9

Determination of the Analgesic Activity

Determination of the Topical Analgesic Activity: the Tail Formalin Test

This test is intended to determine the analgesic activity via topical of global methanol extract (EMG) of *Encella canescens* Lam. The test was performed in not inbred males CF-1 strain mice. The plant extract in study was administered topically, by dipping the tail of animals at a 5% w/v solution of extract in dimethyl sulfoxide (DMSO) for three minutes. Formalin 10%, which is the analgesic agent, is subsequently injected via intradermal in the first third of the tail. Then, the time of licking which makes the mouse at the site of injection for five minutes, was counted. To make possible to count the licking of the mouse he was introduced in a glass chamber, with mirrors on three of its sides, with the aim of optimizing the observation of animals during the count. (Kolesnikov et al, 2004). The same procedure was followed for the control group, in this case the mouse tail was immersed in a solution of dimethyl sulfoxide (DMSO) in the absence of the extract. To calculate the effect, the median of the time of licking±SEM is determined and the median of the treated group with the median of the control group are compared. The topical analgesic activity was calculated using the following formula.

$$\% D = (Cm/Cc) \times 100$$

where:
% D: percentage of pain.
Cm: Median of the time of licking of animals receiving the sample.
Cc: Median of the time of licking of control animals.

Once obtained the % D, the percentage of the topical analgesic activity (% AAT) was calculated.

$$AAT = 100\% - \% D$$

Ibuprofen was used as the reference drug,

Ibuprofen (5% p/v):
% AAT=76.53 percentage of the topical analgesic activity
SEM=6.3

The extract obtained an AAT=52.04%, in comparison with the ibuprofen analgesic activity was lower, therefore as topical analgesic has a lower power with respect to the reference drug.

Determination of Oral Analgesia

To determine the oral analgesic activity of global methanol extract (GME) of *Encelia canescens* Lam, not inbred males CF-1 strain mice were used. This trial evaluated by the method of abdominal twisting induced by acetic acid (algesic agent).

The global methanolic extract, previously dissolved in saline arabic gum 5% was administered through a gastric feeding tube of 4 french, in volumes of 0.4 ml/25 g of mouse weight. After half an hour, an aqueous solution of acetic acid (algesic agent) 0.6% was administered via i.p., the animals were placed individually in a glass chamber, with mirrors on three of its sides, after five minutes began to count the number of twisting (the pain response) compared to the animals in the control group, which only received the vehicle saline arabic gum to 5% and the algesic agent of each of them for five minutes. The analgesic effect was evaluated according to the decrease of abdominal twisting, expressed as a percentage.

To calculate the effect the median of the abdominal twisting±SEM is determined, and the median of the treated group with the median of the control group are compared. Oral analgesic activity is calculated using the following formula.

$$\% D = (Cm/Cc) \times 100$$

where:
% D: Percentage of pain.
Cm: Median of the twisting of animals receiving the sample.
Cc: Median of the twisting of control animals.

Once obtained the % D, the percentage of analgesic effect (% E) was calculated.

$$\% E = 100 - \% D$$

Naproxen sodium was used as the reference drug.

TABLE 10

Topical Analgesia: Assay of the formalin/tail MeOH global extract

| Mouse | seg. | Ranking | % D | % A | Mouse | seg. | Ranking |
|---|---|---|---|---|---|---|---|
| 1 | 4 | 1 | 8.2 | 91.8 | 1 | 34 | 8 |
| 2 | 5 | 2 | 10.2 | 89.8 | 2 | 35 | 9 |
| 3 | 12 | 3 | 24.5 | 75.5 | 3 | 38 | 10.5 |
| 4 | 21 | 4 | 42.9 | 57.1 | 4 | 38 | 10.5 |
| 5 | 26 | 5 | 53.1 | 46.9 | 5 | 42 | 12.5 |
| 6 | 32 | 6.5 | 65.3 | 34.7 | 6 | 42 | 12.5 |
| 7 | 32 | 6.5 | 65.3 | 34.7 | 7 | 45 | 14 |
| 8 | 48 | 15.5 | 98.0 | 2.0 | 8 | 48 | 15.5 |
|  |  |  |  |  | 9 | 50 | 17 |
|  |  |  |  |  | 10 | 52 | 18 |
|  |  |  |  |  | 11 | 57 | 19 |
|  |  |  |  |  | 12 | 58 | 20 |
|  |  |  |  |  | 13 | 63 | 21 |
|  |  |  |  |  | 14 | 65 | 22 |
|  |  |  |  |  | 15 | 80 | 23 |
|  |  |  |  |  | 16 | 94 | 24 |
| n | 8 |  |  |  | m | 16 |  |
| Mean | 22.50 |  | 45.9 | 54.1 |  | 52.56 |  |
| Median | 23.5 |  | 48.0 | 52.0 |  | 49 |  |
| SD | 15.14 |  | 30.89 | 30.89 |  | 16.67 |  |
| SEM | 5.35 |  | 10.92 | 10.92 |  | 4.17 |  |
| W1 | 43.5 |  |  |  |  |  |  |
| % D 1 | 47.96 |  |  |  |  |  |  |
| % A 1 | 52.04 |  |  |  |  |  |  |
| Z1 | −3.4599 |  |  |  |  |  |  |
| P1 | 0.000027 |  |  |  |  |  |  |

TABLE 11

Analgesic effect of methanol extract of *Encelia canescens* Lam 200 mg/kg in arabic gum.

| | SAMPLE | | | CONTROLS | |
|---|---|---|---|---|---|
| Mouse | No. twisting | % Analgesic E. | Ranking | No. twisting | Ranking |
| 1 | 0 | 100.0 | 1 | 15 | 8 |
| 2 | 6 | 67.6 | 2 | 15 | 8 |
| 3 | 10 | 45.9 | 3 | 16 | 11.5 |
| 4 | 11 | 40.5 | 4.5 | 16 | 11.5 |
| 5 | 11 | 40.5 | 4.5 | 16 | 11.5 |
| 6 | 13 | 29.7 | 6 | 17 | 14.5 |
| 7 | 15 | 18.9 | 8 | 17 | 14.5 |
| 8 | 16 | 13.5 | 11.5 | 18 | 16 |
| 9 | | | | 19 | 18 |
| 10 | | | | 19 | 18 |
| 11 | | | | 19 | 18 |
| 12 | | | | 20 | 20.5 |
| 13 | | | | 20 | 20.5 |
| 14 | | | | 22 | 22.5 |
| 15 | | | | 22 | 22.5 |
| 16 | | | | 24 | 24 |
| n | 8 | 8 | m | 16 | |
| Mean | 10.3 | 44.6 | | 18.4 | |
| Median | 11.0 | 40.5 | | 18.5 | |
| SD | 5.2 | 28.0 | | 2.7 | |
| SEM | 1.8 | 9.9 | | 0.7 | |
| W | | | 40.5 | | |

% E with mean 44.4
% E with median 40.5
Median Controls 18.5
Median Sample 11.0
% FINAL E WITH MEDIAN 40.5
z = −3.64
p = 0.0001
z = w − [(n*(m + n + 1))/2]/ROOT[(m*(n*(m + n + 1)))/12]

Naproxen Sodium
% E=70 percentage of analgesic effect.
SEM=4

The extract obtained a % E=405, compared to Naproxen sodium analgesic activity was lower, therefore, as an oral analgesic would have less power (less than 50%) with respect to the reference drug.

Obtaining of specific compounds. In addition to the benzofuran isolated in the first work, a second compound characterized as a flavonoid of the cromanonas family was isolated. These compounds were fully characterized by the registry of its physical and spectroscopic properties.

REFERENCES

Bohlmann, F. Tsankava, E. Jakupovic, J. King, R. M. Robinson, H. 1983. Dimeric chromenes and mixed dimers of a chromene with euparin from *Encelia canescens* Phytochemistry. 22 (2), 557-560.

Brako. L. y J. L. Zarucchi. 1993 Catalogue of the Flowering Plants and Gymnosperms of Peru Monographs in Systematic Botany from the Missouri Botanical Garden 45: i-xl, 1-1286.

Erazo S., Muñoz O., Garcia M., Lemus I., Backhouse N., Negrete R., San Feliciano A., Delporte C., 2002. Constituents And Biological Activities of Muehienbeckia hastulata. *Z. Naturforsch* 57c, 801-804.

Guía Técnica, Diabetes Mellitus tipo 1, MINSAL, 2005, Chile.

Guía Técnica, Diabetes Mellitus tipo 2, MINSAL, 2005, Chile

Hollander, M. Wolfe, D. (1973) Nonparametric Statistical Methods. J. Wiley and Sons, New York, p 27-32, 62-70.

Kolesnikov Y, Cristea M., Oksman G., Torosjan A., Wilson R. 2004. Evaluation of the tail formalin test in mice as a new model to asses local analgesic effects, *Brain Research*, 1029: 217-223

Linares, E. y Benavides M. A 1995. Flora silvestre del transecto Yura-Chivay, Departamento de Arequipa. Boletín de Lima No. 100:211-254.

Linares, E. 2000. Etnobotánica del transecto Yura-Chivay, departamento de Arequipa, Perú., Chloris chilensis revista chilena de flora y vegetación Año 3. No. 1.

Medina E, Kaempffer A. Mortalidad par cancer en Chile: consideraciones epidemiológicas. Rev Méd Chile 2001: 129: 1195-1202.

Moerman. D. 1998. Native American Ethnobotany Timber Press. Oregon.

Pastor S. et al., 1996 Peru: Informe Nacional para la Conferencia Tecnica Internacional de la FAO Sabre los Recursos Fitogeneticos. Leipzig.

Rahalison L., Hamburger M., Hostettmann K., Monad M., Frenk E., 1991. A Bioautographic Agar Overlay Method for the Detection Of Antifungal Compounds From Higher Plants. Phytochemical Analysis, 2, 199-203.

Zuloaga, F. O. y Morrone, O. (editores) (1996) Catálogo de las Plantas Vasculares de la República Argentina. Monographs in Systematic Botany from the Missouri Botanical Garden, Vol. 60.

The invention claimed is:

1. A phyto-pharmacological composition comprising an extract of *Encelia canescens* Lam, wherein said extract contains terpenes, flavonoids, coumarins and tannins, and
   pharmaceutically acceptable excipients;
   wherein said *Encelia canescens* Lam comprises 5-20% of the composition, said terpenes, flavonoids, tannins, and coumarins amount to 0.01 to 5% by weight of the extract, and said composition is used to treat a disease, selected from the group consisting of type I and II diabetes mellitus, hepatomas, brain tumors, leukemias, and/or cancer of pancreas, gastric, prostate, breast, kidney, colon, lung, gallbladder, uterus, the oral cavity, colorectal, or bladder.

2. The composition of the claim 1 wherein the extract is in a solid or liquid state.

3. The composition of the claim 2 wherein the solid state is crystalline extract powder obtained by aqueous or ethanol extraction, lyophilized powder, granules, provisions in solutions, bags, capsules, tablets or pills.

4. The composition of the claim 2 wherein the liquid state is an aqueous or ethanol solution, a syrup or a suspension.

5. The composition of the claim 1 which is administered as oral, sublingual, intradermal, intramuscular, intravenous or by topical route.

6. An extract of the plant *Encelia canescens* Lam, wherein said extract contains terpenes, flavonoids, coumarins and tannins, and pharmaceutically acceptable excipients;

wherein said terpenes, flavonoids, tannins, and coumarins amount to 0.01 to 5% by weight of the extract, and wherein said extract is obtained using water, ethanol or mixtures of them as agents of extraction; and useful for treating a disease selected from the group consisting of type I and II diabetes mellitus, hepatomas, brain tumors, leukemias, and/or cancer of pancreas, gastric, prostate, breast, kidney, colon, lung, gallbladder, uterus, the oral cavity, colorectal, or bladder.

7. The extract according to claim 6 is an ethanol extract.

8. The extract according to claim 6 is an aqueous extract.

9. The composition of claim 1, wherein the composition is included in a phyto-pharmacological agent wherein said agent is useful as an antimicrobial agent.

10. The composition of claim 1, wherein the composition is included in a phyto-pharmacological agent, wherein said agent is useful as antimicrobial against *E. coli, Klebsiella, M. flavus, S. aureus* and *B. subtilis*.

11. The composition of claim 1, wherein the composition is included in a phyto-pharmacological agent, wherein said agent is useful to treat diseases generated by oxidative stress.

12. The composition of claim 1, wherein the composition is included in a phyto-pharmacological agent, wherein said agent is useful to treat neoplastic diseases.

13. The composition of claim 1, wherein the composition is included in a phyto-pharmacological agent, wherein said agent is useful to treat metabolic diseases.

14. The composition of claim 1, wherein the composition is included in a phyto-pharmacological agent, wherein said agent is useful as analgesic.

15. The composition of claim 1, wherein the composition is included in a phyto-pharmacological agent, wherein said agent is useful as a topical or oral analgesic.

* * * * *